(12) United States Patent
Raza

(10) Patent No.: US 9,055,947 B2
(45) Date of Patent: Jun. 16, 2015

(54) DEVICE AND METHOD FOR ANASTOMOSIS

(75) Inventor: Syed Tasnim Raza, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 442 days.

(21) Appl. No.: 12/940,127

(22) Filed: Nov. 5, 2010

(65) Prior Publication Data
US 2012/0116427 A1  May 10, 2012

(51) Int. Cl.
A61B 17/11 (2006.01)
A61B 17/115 (2006.01)

(52) U.S. Cl.
CPC ......... *A61B 17/1155* (2013.01); *A61B 17/1152* (2013.01); *A61B 2017/1107* (2013.01); *A61B 2017/1132* (2013.01); *A61B 2017/1157* (2013.01)

(58) Field of Classification Search
CPC ........... A61B 17/1152; A61B 17/1155; A61B 2017/1157
See application file for complete search history.

(56) References Cited

U.S. PATENT DOCUMENTS

| | | | |
|---|---|---|---|
| 5,188,638 A | 2/1993 | Tazakis | |
| 5,346,115 A * | 9/1994 | Perouse et al. | 227/179.1 |
| 5,720,744 A | 2/1998 | Eggleston et al. | |
| 5,720,755 A * | 2/1998 | Dakov | 606/139 |
| 6,402,008 B1 | 6/2002 | Lucas | |
| 6,540,758 B1 | 4/2003 | Raza | |
| 6,984,238 B2 | 1/2006 | Gifford, III et al. | |
| 7,000,818 B2 | 2/2006 | Shelton, IV et al. | |
| 7,112,212 B2 | 9/2006 | Raza | |
| 7,122,044 B2 * | 10/2006 | Bolduc et al. | 606/219 |
| 8,066,720 B2 | 11/2011 | Knodel et al. | |
| 2008/0082115 A1 | 4/2008 | Morgan et al. | |
| 2009/0138030 A1 | 5/2009 | Gronberg | |

FOREIGN PATENT DOCUMENTS

WO  WO 2008/089404  7/2008

OTHER PUBLICATIONS

Kolvenbach, Ralf, et al., "Evaluation of an Aortic Stapler for an open aortic anastomosis".
International Search Report for PCT/US2013/40171 (WO 2013169921).

* cited by examiner

Primary Examiner — Jonathan W Miles
Assistant Examiner — Todd J Scherbel
(74) Attorney, Agent, or Firm — Walter M. Egbert, III; Hughes Hubbard & Reed LLP

(57) ABSTRACT

Device and method for anastomosis may include a circular stapler with central anvil and multiple circumferentially disposed stapling limbs. A tubular graft may be sleeved on the anvil. The anvil with sleeved graft may be inserted into an end of a dissected aorta to form an overlap. Control actuation may cause the limbs to all substantially simultaneously close and then fire staples respectively into the overlap. The staples may form two generally parallel rows around the overlap with staples of each row being staggered relative to staples of the other row, thereby making a leak-free connection between the tubular graft and the end of the aorta. Control actuation may cause the limbs to open so the anvil may be removed from the end of the aorta, leaving the tubular graft in a leak-free connection with the aorta's end. Exemplary embodiments may allow for generally faster anastomosis than prior art.

21 Claims, 12 Drawing Sheets

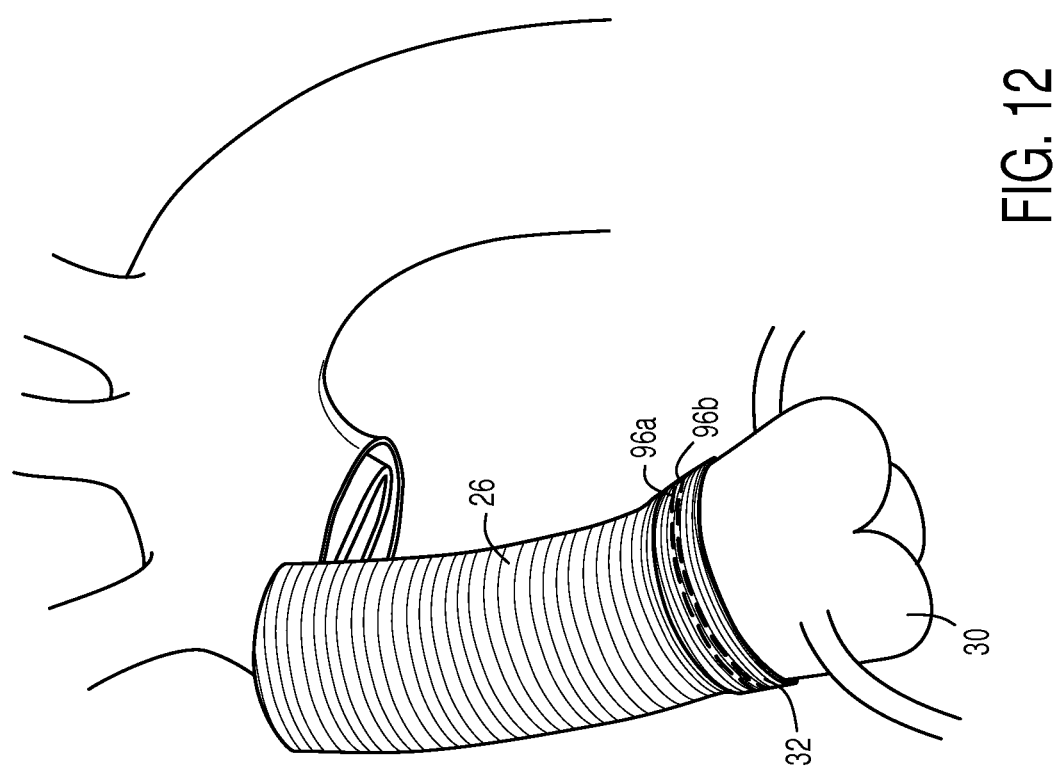

DEVICE AND METHOD FOR ANASTOMOSIS

FIELD OF THE INVENTION

The invention relates generally to the field of surgery and particularly to surgical suturing devices and methods.

BACKGROUND

A heart is illustrated in FIG. 1, and is generally designated by the reference letter H. The heart H includes a right atrium RA, a left atrium LA, a right ventricle RV, a left ventricle LV, a pulmonary artery PA, and an aorta A. The aorta A includes an intimal (inner) layer or intima IL (FIG. 2) and an adventitial (outer) layer or adventitia AL.

In Type A aortic dissection, the intimal (inner) layer or intima IL is torn and defines a tear T in the ascending aorta AA or aortic arch. Blood B collects in (unnumbered) between the layers AL, IL. This is referred to as a false lumen. If the blood collection continues, the false lumen may block off origin of major arteries coming off the aorta, thus causing abrupt lack of blood flow to the involved organ, causing its death. This condition may be fatal, or cause of major morbidity, if not treated urgently.

Treatment may necessitate dissection of an aortic portion AP of the aorta A containing the portion with intimal tear along lines of dissection LD1, LD2, and replacement of the cutout portion of the aorta by a Dacron® tube graft of appropriate size. More particularly, the dissection along lines of dissection LD1, LD2 may separate a distal end or end portion Ea of the ascending aorta AA from a proximal end or end portion Ed of the ascending aorta AA. The two ends or end portions Ea, Ed of the ascending aorta AA, after the dissected aorta portion AP and particularly the intimal portion thereof has been excised, are still quite fragile and the two layers AL, IL are still separated. The two ends Ea, Ed may be prepared for the Dacron® tube graft by suturing the respective ends Ea, Ed and buttressing them with strips of Dacron® or felt both on the inside and the outside of the ends Ea, Ed. After both ends Ea, Ed are prepared, the Dacron® tube graft is anatamosed to restore the continuity of the aorta and establish blood flow.

The treatment described above may take a considerable length of time using prior art methods and devices. During the treatment, the patient is on cardiopulmonary bypass (heart-lung) machine. For part of the time, all circulation is stopped. On average, a patient may be on the heart-lung machine for three hours and 20 minutes, and the average time of a patient's circulation being stopped is 34-40 minutes. The lengths of these times contribute to the increased risk of stroke, bleeding, and death. In particular, at the time of preparation of this material, the operative mortality rate is 17.84%, post-op neuro deficit is 10.3%, and re-exploration for bleeding is 16.5%. Thus, there is need to reduce the length of time that it takes to carry out the treatment of replacing a cutout portion of the aorta with a tube graft of appropriate size.

SUMMARY

Generally stated, the invention relates to apparatuses and methods for anastomosis. An exemplary embodiment provides a circular stapler that may be used for anastomosis such as between the end of a dissected aorta and the end of Dacron® tube graft. Features and actions of the exemplary embodiments allow for generally faster anastomosis than with prior art devices and methods as explained below.

The invention may be embodied as an apparatus of a relatively small design advantageous for use in the limited space of the operative field. An exemplary device according to the invention may be a single unit including the anvil and stapling heads. The single unit design may reduce alignment complexity and problems compared to working with other devices where the anvil and stapling head may be separate units. The exemplary device requires only generally minimal dexterity for operation—an advantage especially in a confined space—at least because the device may be actuated by simply turning or actuating a control knob. Moreover, there may need to be only a single actuation to accomplish multiple staple firings.

Time savings are additional advantages. Use of the invention in exemplary devices and methods may save critical time during anastomosis procedures. One way in which time is saved is that the invention does not require "cuffing" of the end of the aorta for stapling to the graft. The invention also saves time in that embodiments do not require a series of many stapling actions. Rather, the invention may provide for single actuation of multiple simultaneous stapling or simultaneous multi-fire stapler actuations. The results of the concurrent stapling actions by the single actuation of an embodiment of the device include a leak-free seal of the materials stapled. The single actuation of the device that results in the simultaneous multiple staples being fired provides for accurate alignment of the staples for the precise closure required for the leak-free connection of the materials.

Using exemplary embodiments, the user may avoid or at least minimize the use of sutures in anastomosis and the problems caused by sutures. In previous embodiments, sutures were often pulled "tight" to affect a seal, but such pulling could lead to tearing delicate tissues and further bleeding. In contrast, the multiple staples fired by exemplary embodiments in a single action into the materials to be connected form a strong leak-free connection thereof. The embodiments' firing of staples into two rows according to the interleaved or staggered pattern may provide higher bonding and leak resistance than connections made by prior art devices and methods. Further, the simultaneous firing of multiple staples may have the advantage of a single pressure action during the anastomosis process rather than multiple pressure actions when applying individual sutures or staples in series.

An exemplary apparatus according to the invention includes an anvil with stapling limbs. The anvil may be generally cylindrical. The limbs are disposed generally circumferentially about and along the length of the anvil. Each limb has stapling functionality at its end corresponding to the front end of the anvil. A limb end of the stapling limb may be moved from an open position at a distance from the front end of the anvil to a closed position closer to the front end of the anvil. The exemplary apparatus also includes a cam for causing movement of each limb end from its open position to its closed position. A control on the exemplary apparatus may be selectively activated to cause the cam to cause the movement of each limb end to its closed position. This embodiment may include a cam that is also disposed for causing a movement of each limb end from its closed position to its open position, and a control that is also capable of being selectively activated to cause the cam to cause the movement of each limb end to its open position.

The anvil of this exemplary apparatus may receive a graft for connection to a vessel. The graft may be tubular and may be sleeved over the cylindrical anvil. The anvil may be sized for different graft diameters, and the graft may be secured to the anvil by a tie.

In the operative field, at least a part of the anvil with the graft may be inserted into a portion of the vessel to create an overlap of the graft and the vessel on the anvil. A user may activate the control to cause the cam to cause each limb end in its closed position to fire at least a staple into the overlap on the anvil to make a connection between the vessel and the graft at the overlap. The connection may be a substantially leak-proof connection. The staples may be fired into the overlap to form two generally parallel rows in the overlap with staples of each row being staggered with respect to staples of the other row. The staples may be fired into the overlap substantially all at once.

More particularly, the stapling limbs of the exemplary embodiment may be disposed in pairs with each of the limb ends in a pair firing three staples in two rows into the overlap. A first limb end of the pair may fire a staple into a top row and two staples into a bottom row, the two staples in the bottom row being spaced apart, and the staple in the top row positioned generally parallel at least in part to the space between the two staples in the bottom row. A second limb of the pair may fire two staples into a top row and one staple into a bottom row, the two staples in the top row being spaced apart, and the staple in the bottom row positioned generally parallel at least in part to the space between the two staples in the top row.

This embodiment may accommodate the positioning of a strip of material over at least a segment of the portion of the vessel that is included in the overlap prior to the firing of staples into the overlap. If the strip of material is included, then it is connected to the overlap by the fired staples.

Another exemplary embodiment may take the form of a device for substantially leak-free fastening of at least two tubular elements. The device may include a generally cylindrical central base having a fastening end. The device also may include a fastening mechanism positioned about the fastening end of the base. The fastening mechanism may be capable of moving between an open position about the fastening end and a firing position about the fastening end. The open position of the fastening mechanism allows substantially an entire length of a tubular first element to be sleeved relatively snugly around the base of the device. The open position of the fastening mechanism also allows for insertion of the fastening end of the base into a portion of a tubular second element. When the fastening end with sleeved tubular first element is inserted into the portion of the tubular second element, an overlap is formed. The fastening mechanism of this exemplary device is responsive to a firing actuation to move from its open position into the firing position about the fastening end and substantially close to the overlap, and to make a circumferential substantially leak-free fastening between the first and second tubular elements at the overlap. The fastening mechanism also may be responsive to an opening actuation to move away from the firing position to allow for withdrawal of the fastened first and second tubular elements from the base. In addition, the fastening mechanism may be responsive to a positioning actuation to move from the open position into a closed position about the fastening end and substantially close to the overlap.

Another exemplary apparatus for anastomosis may include a means for supporting a generally cylindrical graft for connection to a generally cylindrical vessel. The vessel may have a diameter slightly greater than a diameter of the graft. The means for supporting may be configured so that at least a part of the graft may be slipped into at least a portion of the vessel to form an overlap of the portion of the vessel over the part of the graft. The exemplary embodiment also may include means for making a substantially leak-proof connection between the graft and the vessel at the overlap to form a connected graft and vessel.

The invention also provides for methods. An exemplary method for anastomosis includes the action of positioning a tube to fit around a cylindrical anvil of a circular stapler. The tube may be secured to the anvil. The stapler may include stapling arms in a radial distribution. With the stapling heads of the stapler in an open position relative to the anvil, the anvil is inserted into a dissected end of an aorta. In particular, the insertion is accomplished so that a segment of the tube underlies a part of the dissected end of the aorta to form an overlap between the tube segment and the end part of the dissected aorta. In this exemplary method, the stapling heads may be caused to move into a firing position relative to the anvil inside the overlap. This firing position also may be a radial distribution of the stapling heads about the overlap. The stapling heads may be caused to fire staples in two parallel rows around the overlap to form a leak-free connection between the tube and the dissected end of the aorta. Each staple may pierce the overlap and may at least partially close behind it by a closing interaction between each staple and the anvil (or otherwise). The closing interaction may be an inward movement of each leg of a staple when it encounters the anvil.

After stapling, the stapling heads may be caused to return to the open position relative to the anvil and the overlap. The tube may be unsecured from the anvil. The anvil may be withdrawn from the tube with the result that the tube remains connected to the aorta at the overlap.

Another exemplary method according to the invention provides for anastomosis of a sleeve and a tubular structure using a circular jawed stapler having a central cylindrical base and stapling heads distributed symmetrically about the base. The actions may include insertion of the base into the sleeve so the sleeve is between the base and the stapling heads. The tubular structure is positioned over the sleeved base so the tubular structure is between the sleeved base and the stapling heads. The stapling heads staple the sleeve and the tubular structure where they overlap to make a leak-free connection. After stapling, the base may be removed from the sleeve through an end of the sleeve opposite to its connection to the tubular structure. The sleeve remains in the leak free connection to the tubular structure.

The nature of the invention will be more clearly understood by reference to the following detailed description and the several views illustrated in the accompanying drawings, but the scope of the invention is not to be limited except by the claims provided below.

BRIEF DESCRIPTION OF THE DRAWINGS

FIG. 12 is an illustration of exemplary results of use of an exemplary embodiment of the invention in connecting a graft with an end of an aorta.

DETAILED DESCRIPTION

Generally stated, the invention relates to a device and method for making a leak-proof connection between a first element and a second element. The invention is described below by reference to exemplary embodiments, but the invention should not be limited by such embodiments or examples provided. The inventions, however, can be embodied in many different forms and carried out in a variety of ways, and should not be construed as limited to the embodiments set forth in this description and/or the drawings. The exemplary embodiments that are described and shown herein are only some of the ways to implement the inventions. Elements and/or actions of the inventions may be assembled, connected, configured, and/or taken in an order different in whole or in part from the descriptions herein.

Figures 1, 2:
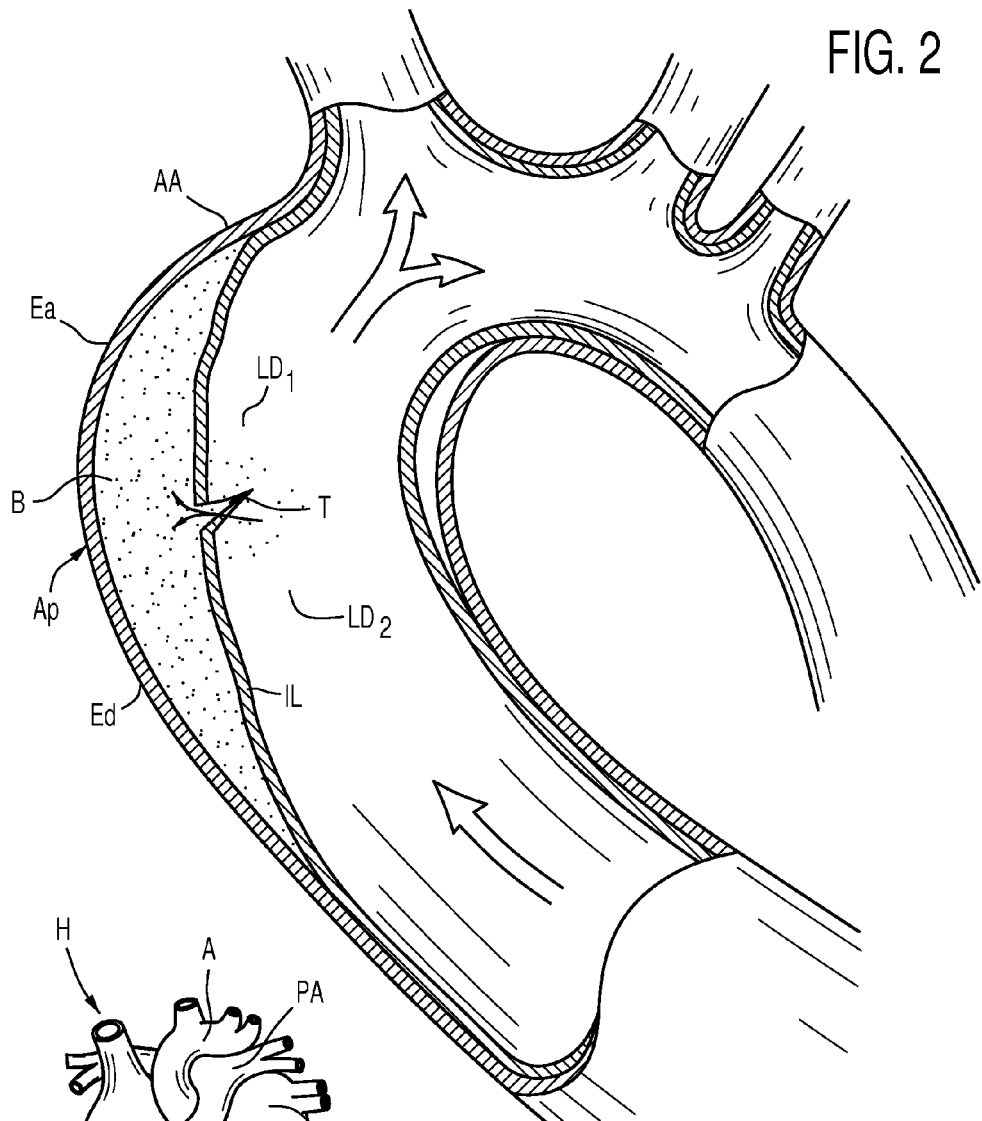
FIG. 1 is a perspective view of a human heart, and illustrates various portions thereof, including the aorta.
FIG. 2 is a highly enlarged perspective view of the aorta of FIG. 1 with portions broken away for clarity, and illustrates intimal and adventitial layers thereof, including an intimal tear in the intima or inner layer of the aorta.
Figure 3:
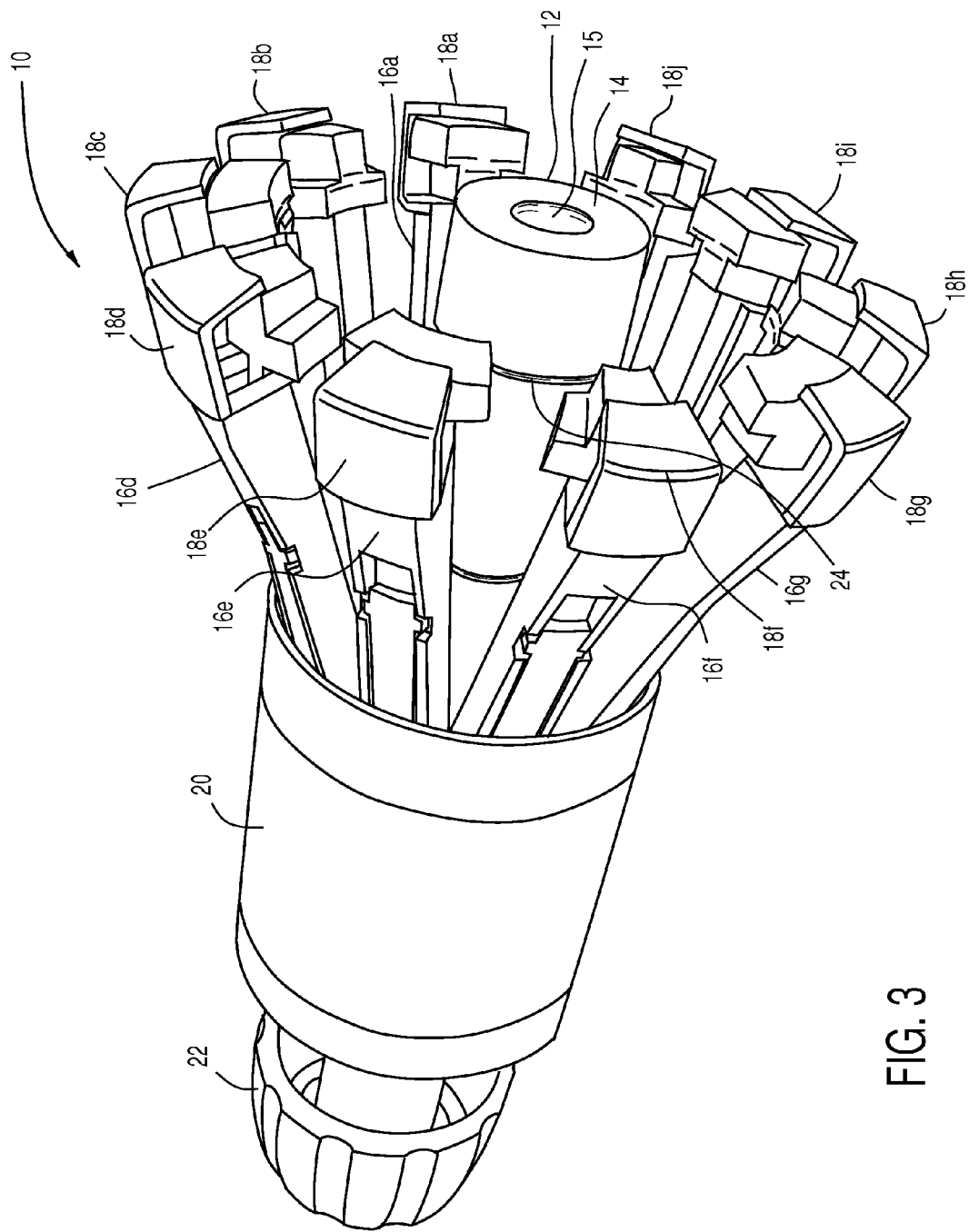
FIG. 3 is a perspective view of an embodiment of the invention.

FIG. 3 illustrates an exemplary embodiment 10 of the inventions as a device that may be used for anastomosis between the generally circular end of a dissected aorta and a tubular graft of an appropriate size. For convenience, this exemplary embodiment 10 may be referred to as a "circular aortic stapler" or "stapler". An overview of the exemplary embodiment 10 is provided in the paragraph immediately below with additional details in the paragraphs that follow. The term "device" is used herein synonymously with the term "apparatus".

In sum, the exemplary embodiment 10 in FIG. 3 includes a central cylindrical anvil 12 with limbs 16a-16j splayed in a generally circular fashion about the front end 14 of the anvil 12 when the embodiment 10 is in the open position, such as when ready for use. Generally stated, to use the embodiment 10, a tubular graft 26 may be positioned over and along the cylindrical central anvil 12 of the exemplary embodiment 10. The graft 26 (not shown in FIG. 3, see FIG. 4) may be said to be "sleeved" on the anvil 12. To use the exemplary stapler 10 in the operative field, the anvil 12 with the tubular graft 26 may be positioned inside one end of the dissected aorta so the end of the aorta lies between the splayed limbs 16a-16j of the stapler 10 and the anvil 12 with tubular graft 26. When the exemplary embodiment is activated, the limbs 16a-16j move from their respective open positions to closer positions relative to each other and to and about the front end 14 of the anvil 12. The embodiment 10 may be further activated to cause the limbs 16a-16j to staple the end of the aorta to the tubular graft 26 at the overlap between the two on the anvil 12. The stapling effects a substantially leak-free connection between the end of the dissected aorta and the tubular graft 26. To remove the exemplary stapler 10, its limbs 16a-16j may be caused to open and the anvil 12 may be slid from the connected aorta and graft without disturbing the leak-free connection there between.

More particularly described, the exemplary embodiment 10 shown in FIG. 3 includes an anvil 12 at its center. The anvil 12 may also be referred to as a base, or a graft support means.

In this example 10, the anvil 12 is generally cylindrical having a length from a front end 14 to a back end (not shown in FIG. 3). Also in this example, the anvil 12 includes a hollow core 15 (to at least partially accept a control screw (not shown in FIG. 3)). The anvil 12 may be made of stainless steel (and/or other appropriate material). The size of the anvil may vary depending on the size of the tubular graft to be used with the anvil. The size of the tubular graft, in turn, may vary depending on the size of the end of the dissected aorta with which the tubular is to be connected. Thus, the size of the anvil may vary depending on the size of the end of the dissected aorta to which the tubular graft is to be connected in a leak-proof manner.

In the exemplary embodiment 10, limbs 16a-16j are disposed about the length of the anvil 12. A limb also may be referred to as an arm, a splay arm, a (or part of) a fastening mechanism, or a (or part of a) leak proof connection means.

In this example, the limbs 16a-16j are disposed generally circumferentially about and along at least some part of the length of the anvil 12. The limb disposition also is generally symmetrical about the anvil 12 in the embodiment 10. Each limb 16a-16j may be made of stainless steel (and/or any other appropriate material). Generally, the size and length of each limb is approximately the same in this embodiment, and such features may depend on the size of the anvil 12. The exemplary embodiment 10 includes ten (10) limbs 16a-16j, but the number of limbs may vary depending upon the embodiment of the invention.

Each limb 16a-16j in this embodiment 10 includes a stapling head 18a-18j at a limb end corresponding to the front end 14 of the anvil 12. A stapling head may be referred to as a stapling arm or a firing head.

Each stapling head 18a-18j of this exemplary embodiment 10 is disposed for movement from an open position about the front end 14 of the anvil 12 to a closed position closer to the front end 14 of the anvil 12. The stapling heads 18a-18j move as a group; they do not move individually between open and closed positions in this embodiment. Other embodiments may vary. Given the radial disposition of the limbs 16a-16j, the open position of the stapling heads 18a-18j has a greater diameter (or radius) than their closed position. In other words, the stapling heads 18a-18j move from their respective open positions in wider circular pattern to closed positions in a smaller circular pattern about the front end 14 of the anvil 12. A stapling head 18a-18j may be made of the same material as its respective limb 16a-16j, or may be made of a different material. In this example 10, the stapling heads 18a-18j are of two types, which are described below.

The exemplary embodiment 10 includes a cam 20 that may be actuated by a control 22. The cam 20 may be actuated to cause the stapling heads 18a-18j to move from their respective open positions to their closed positions.

Depicted in its first or open position in FIG. 3, the cam 20 includes a generally cylindrical element encircling the limb ends opposite the stapling heads 18a-18j and the end of the anvil 12 opposite its front end 14. The generally cylindrical element may be referred to as a sleeve or a clamp sleeve. The clamp sleeve of the cam 20 may be disposed to move along the lengths of the limbs 16a-16j and anvil 12 towards a closed or second position closer towards the stapling heads 18a-18j of the limbs and the front end 14 of the anvil 12. For ease of description herein, the "cam" is said to move rather than the "clamp sleeve of the cam". As the cam 20 moves towards its closed position, the stapling heads 18a-18j may be caused to move from their open positions towards their closed positions about the front end 14 of the anvil 12. The cam 20 may be made of stainless steel (and/or any other appropriate material). The size of the cam is variable so long as it achieves its function.

A control 22 is shown in FIG. 3 as positioned at the end of the embodiment 10 opposite to the front end 14 of the anvil 12, but in other embodiments, the control 22 may be otherwise positioned. The control 22 may be referred to as a rotary control, controller, control knob, knob, OR fire and release knob.

In this embodiment 10, the control 22 may be used to cause the exemplary embodiment 10 to assume its closed position, to fire staples against the anvil 12, and to move to its open position. Particularly, actuating the control 22 by turning it clockwise causes the cam 20 to move from its open position towards its closed position closer to the front end 14 of the anvil 12, thereby causing the stapling heads 18*a*-18*j* to move from their respective open positions to their closed positions closer about the front end 14 of the anvil 12. Also in this embodiment 10, further actuating the control 22 by continued turning clockwise causes the stapling heads 18*a*-18*j* to fire their respective staples against the side of the anvil 12. The control 22 additionally may be used to return or to move the exemplary embodiment 10 to its open position by causing movement of the cam 20 away from the front end 14 of the anvil 12 so that the stapling heads 18*a*-18*j* may move from their small circular pattern about the front end of the anvil 12 to their respective wider circular pattern further from the front end 14 of the anvil 12.

As noted above, the exemplary circular aortic stapler 10 may be used to connect a tubular graft to an end of a dissected aorta. A tubular graft may be made of DACRON® in whole. Other embodiments may have tubular grafts of other materials in whole or in part. A tubular graft also may be referred to as a graft, tube, or sleeve.

The following paragraphs provide an overview of how a tubular graft may be positioned on the stapler 10 prior to moving the stapler 10 with tubular graft for connection to the end of the aorta.

FIG. 3 illustrates the central cylindrical anvil 12 of the exemplary stapler 10. The anvil 12 includes an optional feature, e.g., a contour, to aid in holding a tubular graft in place around the anvil 12. In particular, the anvil 12 includes a groove 24 around a circumference of the anvil 12.

In this example 10, the circumferential groove 24 is generally perpendicular to the longitudinal axis of the anvil 12. The groove 24 is generally "u" shaped in cross-section. The groove 24 has a depth to accommodate the diameter of a tie that may be used with the groove 24 to aid in holding the tubular graft in place on the anvil. Alternatively, the groove 24 may have more or less depth than the diameter of a tie that may be used coordinately with the groove 24, may be of a different shape in cross section, and/or may be positioned differently so long as the groove 24 at least partially carries out its function in aiding the tubular graft to stay in place on the anvil 12. Other embodiments of the invention may forego the use of a feature such as the groove 24 and/or ties.

In the exemplary embodiment 10 shown in FIG. 3, the groove 24 is positioned generally at a distance latitudinally away from the front end 14 of the anvil 12 so as not to interfere or be aligned with the stapling connection made between the tubular graft and the end of the dissected aorta. The groove 24 may be positioned on the anvil so the groove 24 is not covered by the part of the end of the dissected aorta that is positioned over a section of the tubular graft covering the anvil 12.

Figure 4:
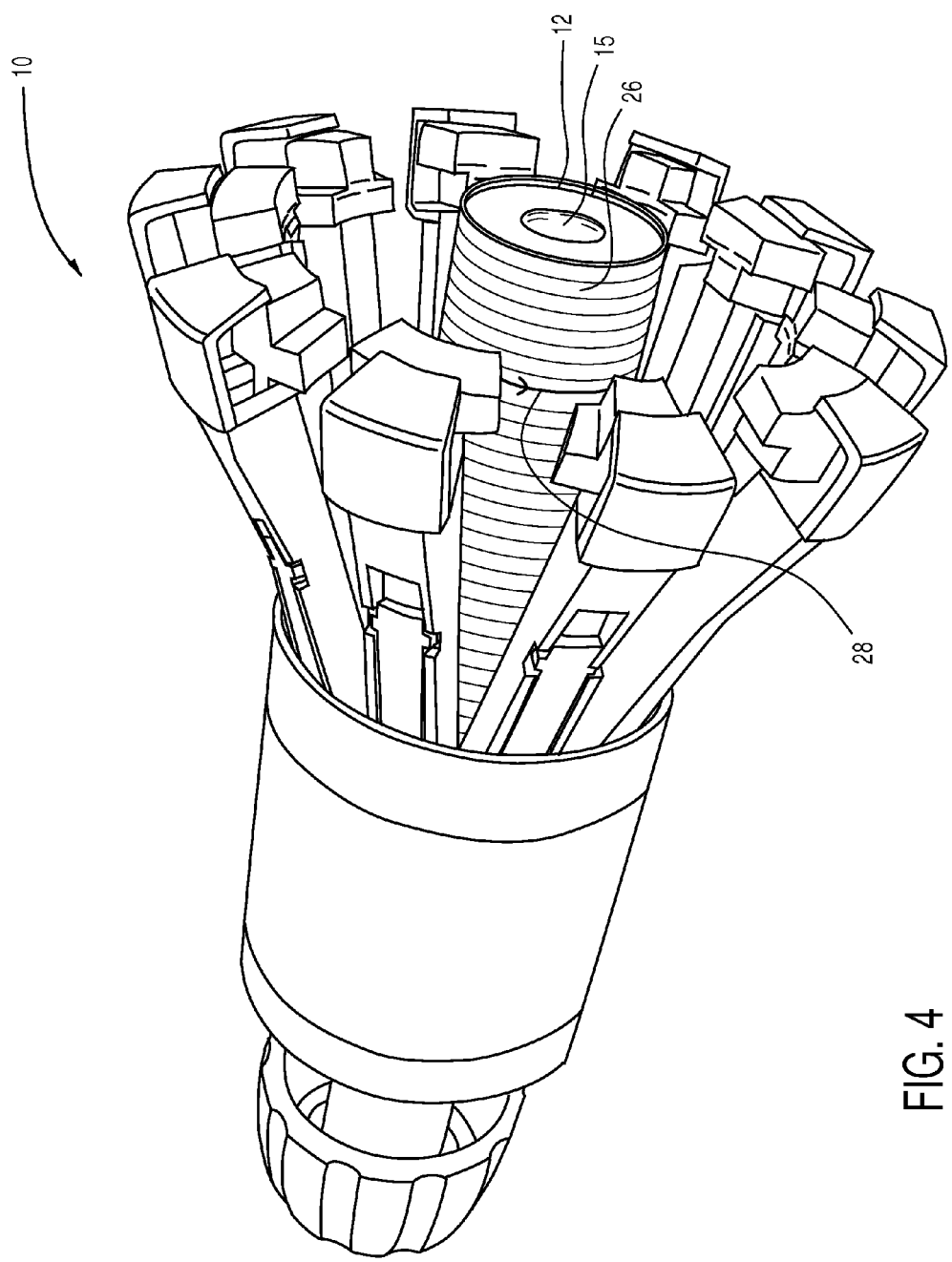
FIG. 4 is a perspective view of the embodiment of FIG. 3 with the addition of a secured graft.

FIG. 4 shows the same exemplary embodiment 10 as in FIG. 3, but the entire length of a tubular graft 26 is now sleeve-fitted over the anvil 12. Particularly, the tubular graft 26 may be fitted over the anvil by inserting the front end 14 of the anvil 12 into an end of the tubular graft 26 (not shown) and drawing the tubular graft 26 along the length of the anvil 12 until substantially the entire length of the tubular graft 26 covers the anvil 12. A front end of the tubular graft 26 may align with the front end 14 of the anvil 12, but that does not necessarily have to be the case.

The fit between the tubular graft 26 and the anvil 12 is generally snug in this embodiment 10. In other words, the diameter of the cylindrical anvil 12 may be just slightly less than the diameter of the tubular graft 26. The snug fit may be enough to hold the tubular graft 26 in place around the anvil 12. The exemplary embodiment 10, however, as explained above, includes a feature to help hold the graft 26 in place around the anvil 12. The feature includes the circumferential groove 24 on the anvil 12 shown in FIG. 3.

FIG. 4 shows how the groove 24 around the anvil 12 of the exemplary embodiment 10 may be used to aid in keeping the tubular graft 26 in place around the anvil 12. A tie 28 may be used to tie the tubular graft 26 to the anvil 12. In particular, the tie 28 is tied around the tubular graft 26 and anvil 12 at a position generally above or corresponding to the groove 24 on the anvil 12. The tie 28 may be tied tight enough so the tie 28 when fixed does not add much if any diameter to the combination of the anvil 12 with groove 24, tubular graft 26, and tie 28. To put it another way, the secured tie 28 may lie along with the tied portion of the tubular graft 26 generally in the circumferential groove 24 around the anvil 12. The tie 28 may be fixed in any manner appropriate and that may allow for its easy release so the tubular graft 26 may be pulled away from its position around the anvil 12 of the aortic stapler 10.

The tie 28 in the embodiment 10 may be made of suture string, thread, or other material, and may be hand tied. Alternatives to the tie 28 and its characteristics are possible. In addition, an embodiment of the invention may make use of a tie 28 (or an alternative) as an aid to holding a tubular graft in place on an anvil of an aortic stapler, but that embodiment may lack the groove 24 shown in FIG. 3 (or have an alternative feature to the groove).

With the tubular graft 26 attached to the anvil 12, the exemplary stapler 10 is ready to be moved into the operative field so the graft 26 may be connected to an end of the dissected aorta. In particular, the exemplary stapler 10 is positioned so part of the anvil 12 with the tubular graft 26 is inserted into the end of the dissected aorta. The insertion of part of the anvil 12 with the tubular graft 26 causes an overlap between part of the tubular graft 26 and a portion of the dissected end of the aorta.

Figure 5:
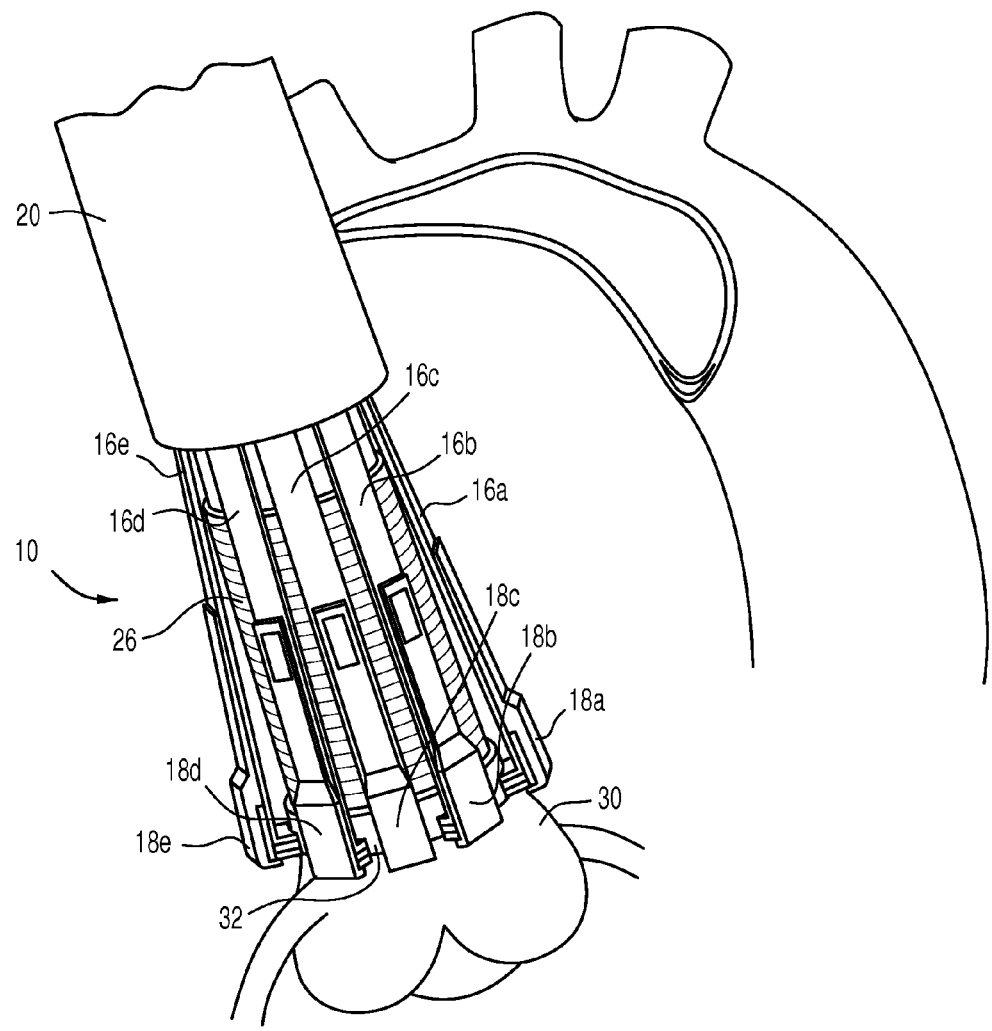
FIG. 5 is a perspective view of part of the embodiment of FIG. 3 as it may be in use in the operative field.

FIG. 5 illustrates part of the same embodiment 10 of FIGS. 3 and 4, but FIG. 5 shows the exemplary stapler 10 as it may be initially positioned in the operative field with respect to an end of a dissected aorta 30 to which the tubular graft 26 sleeved over the anvil 12 is to be connected in a leak-proof manner.

Prior to the positioning shown in FIG. 5 of the exemplary stapler 10 with sleeved tubular graft 26 with respect to the end of the dissected aorta 30, a collar of graft or graft collar may be positioned around the end of the dissected aorta 30. The graft collar 32 may be used to reinforce the end of the dissected aorta 30. The graft collar 32 may be made of DACRON®. Other embodiments may be made in whole or in part of other materials. The graft collar 32 also may be referred to as a reinforcement ring.

Referring again to FIG. 5, the positioning of the exemplary stapler 10 with sleeved tubular graft 26 is described with respect to the end of the dissected aorta having the encircling graft collar 32. In particular, the exemplary stapler 10 with sleeved tubular graft 26 is moved into the operative field so the front end of the anvil 12 with tubular graft 26 is inserted into the end of the dissected aorta 30 with graft collar 32. Specifically, the end of the aorta 30 with graft collar 32 overlaps the part of the tubular graft 26 covering the end of the anvil 12 inserted into the end of the dissected aorta 30. The overlap is positioned between the stapling heads 18a-18j of the limbs 16a-16j of the exemplary stapler 10 and the end of the anvil 12 inserted into the end of the dissected aorta 30.

Figure 6:
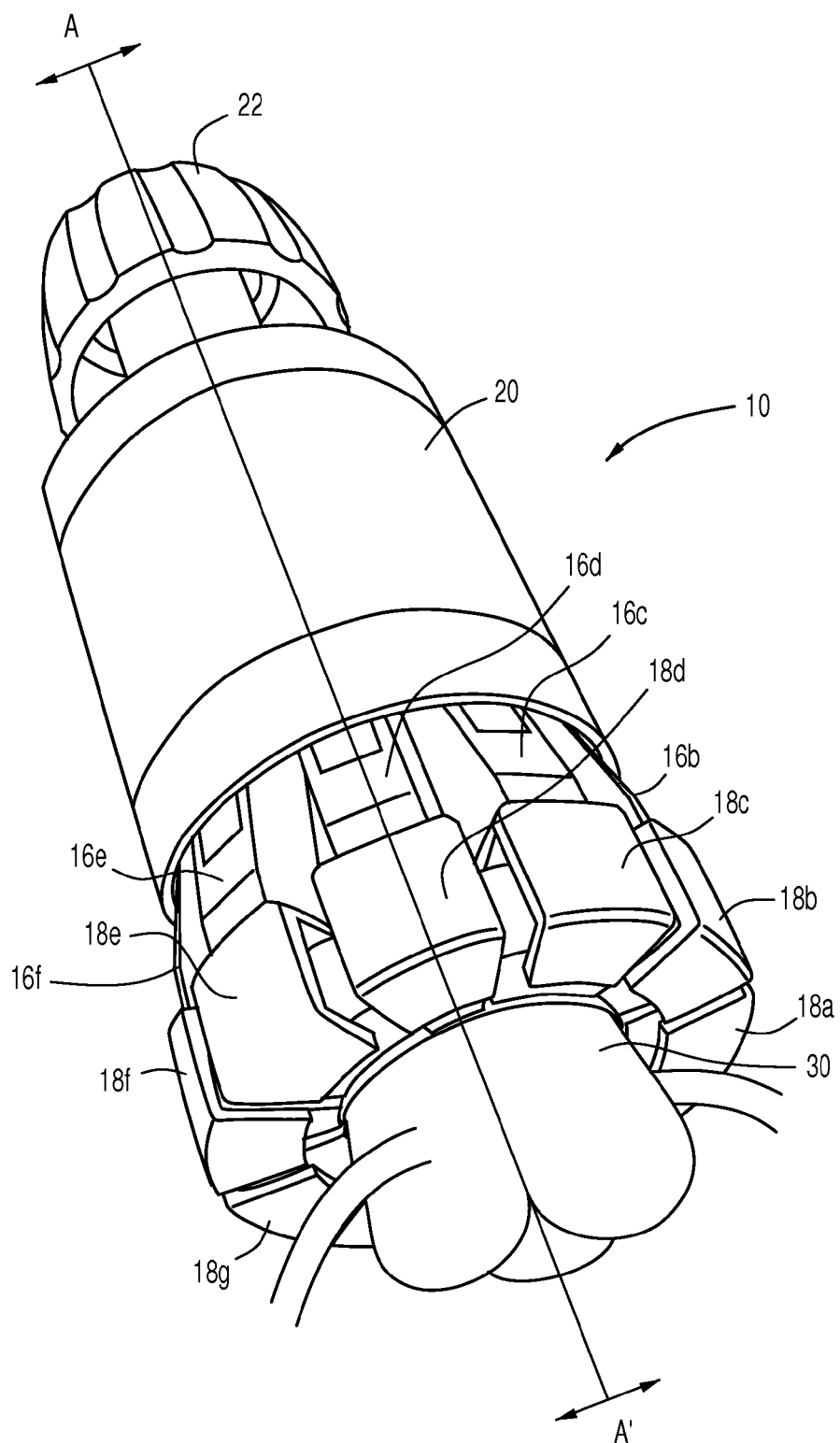
FIG. 6 is a perspective view of the embodiment of FIG. 3 as it may be in use in connecting a graft to an end of an aorta.
Figure 7:
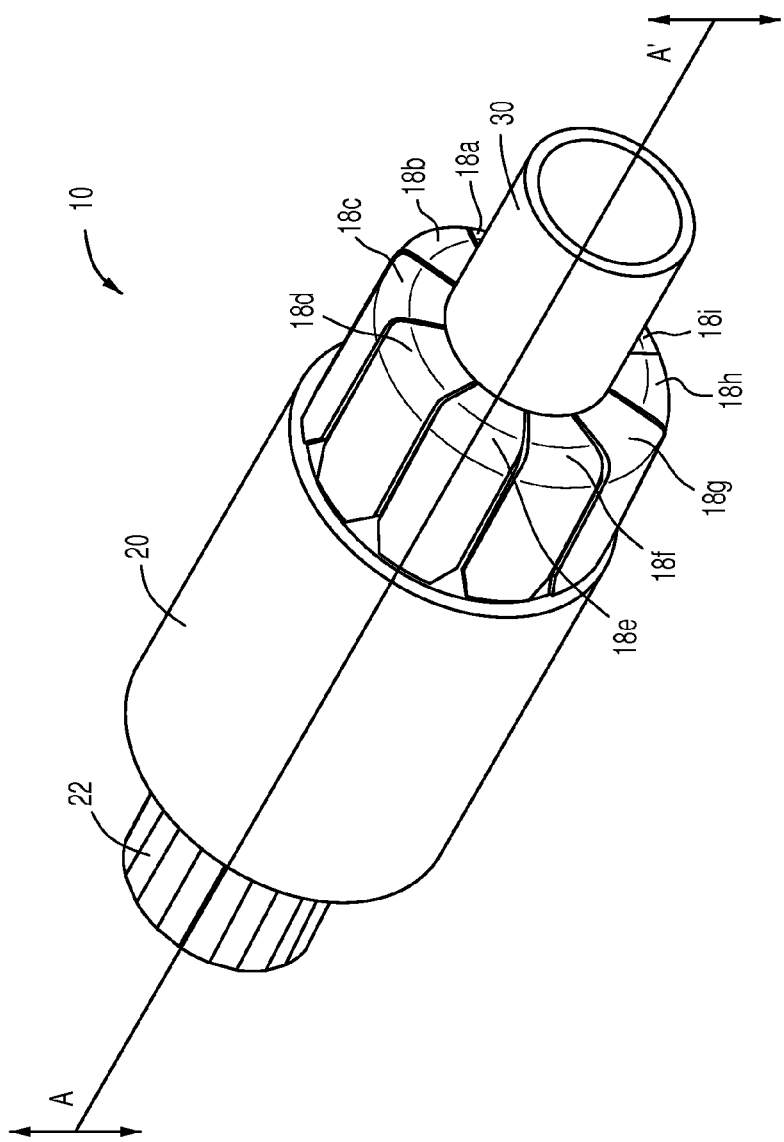
FIG. 7 is a perspective view of the embodiment of FIG. 3 with the limbs of the embodiment in a closed position.

Once the exemplary stapler 10 and the end of the dissected aorta 30 with graft collar 32 are positioned so that a portion of the end of the dissected aorta 30 with graft collar 32 lies below the stapler's 10 stapling heads 18a-18j, but above the end of the tubular graft 26 covering the anvil inserted into the end of the dissected aorta 30, the exemplary stapler 10 may be moved from its open position (as shown in FIG. 5) to a closed position (as shown in FIG. 6) and then to a firing position (as shown in FIG. 7). Some embodiments may omit the closed position, instead moving from an open position to firing position. Other embodiments may have more than the listed positions. In some embodiments, the closed position may be the same as the firing position, but a specific actuation may be necessary to fire the staples rather than an automatic firing once the stapler moves into that position.

In its open position (as shown in FIG. 5), the cam 20 is furthest from the front end 14 of the anvil 12 of the exemplary stapler 10. To reach its closed position (as shown in FIG. 6), the cam 20 slides along the lengths of the limbs 16a-16j in a longitudinal direction towards the front end 14 of the anvil 12. As the cam 20 slides towards the front end 14 of the anvil, the cam 20 acts on the limbs 16a-16j so the stapling heads 18a-18j move closer towards each other and the front end 14 of the anvil 12. The action of the cam 20 on the limbs 16a-16j may be a lever action. In their closed position, the stapling heads 18a-18j have little if any space between as may be seen in FIG. 6.

From its closed position as shown in FIG. 6, the exemplary stapler 10 may be moved to its open position as shown in FIG. 5 or to its firing position as shown in FIG. 7. Other embodiments may provide other positions so those embodiments may provide other options.

In this embodiment, the stapler 10 may be moved to its open position by turning the control 22 in a counterclockwise direction to cause the cam 20 to slide back the way it came and away from the front end 14 of the anvil 12. In particular, the cam 20 may be provided with spring rods to provide reverse tension on the limbs (also referred to as the firing sleeve arms) as the clamp sleeve of the cam is retracted after firing.

Also in this embodiment, the stapler 10 may be moved into its firing position by further turning the control 22 in the clockwise direction. Turning the control 22 in such a way causes the cam 20 to interact with the limbs 16a-16j so they carry out a stapling function. Particularly, turning the control 22 further in the clockwise direction causes the cam 20 to continue its sliding movement from its closed position further towards the front end 14 of the anvil 12. The cam's continued movement towards the front end 14 causes the stapling heads 18a-18j of the limbs 16a-16j to move into firing position as shown in FIG. 7, and to fire their respective staples.

Figure 8:
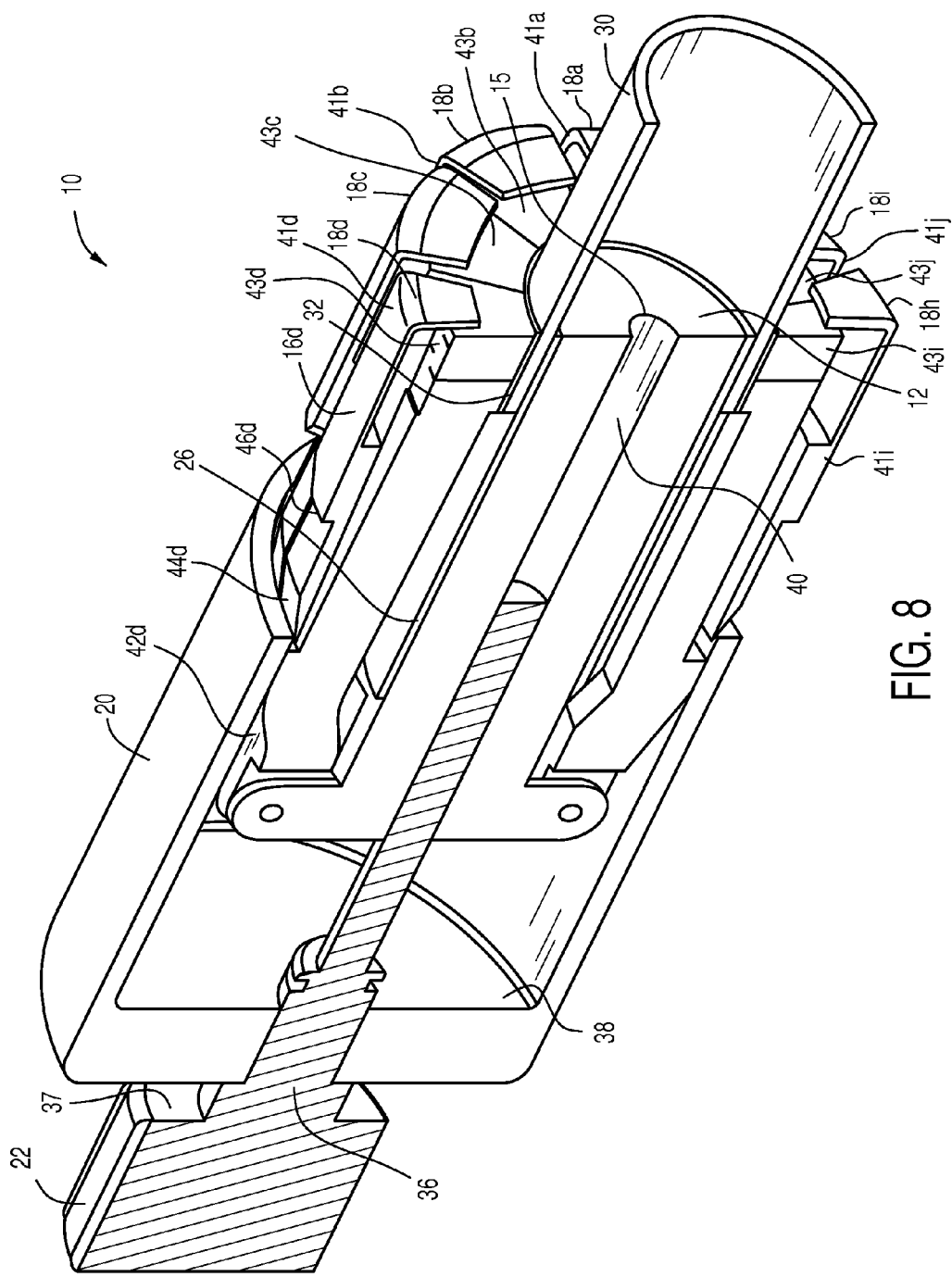
FIG. 8 is lengthwise cross section view of the embodiment shown in FIG. 7 taken along the line defined by A-A' in FIG. 7.

FIG. 8 is a cut-away diagram showing the interior of the exemplary stapler 10 for use in explaining the motion of the cam 20 with respect to other elements The cut-away diagram is taken along lines A-A' marked in FIGS. 6 and 7. The cut-away diagram illustrates the exemplary embodiment 10 in its closed position.

In particular, FIG. 8 shows that a control screw 36 protrudes from the side 37 of the control 22 closest to the cam 20. The control screw 36 passes through a central hole in the side face 38 of the cam 20. The side face 38 of the cam 20 is facing the side 37 of the control 22. The side face 38 is generally perpendicular to the longitudinal axis of the cam 20. After passing through the side face 38 of the cam 20, the control screw 36 fits into a central shaft 40 of the anvil 12. The control screw 36 is connected to the central shaft 40 by a slip joint which allows the control screw 36 to rotate and force motion of the cam without turning the anvil 12. When the control 22 is turned, the control screw 36 turns and causes the cam 20 to move either towards the front end 14 of the anvil 12 or away from the front end 14.

FIG. 8 also shows the movement of the cam 20 on the respective tops of the limbs 16a-16j and the spring angle tension there between. Segments of the respective tops of the limbs 16a-16j come into contact with the underside of the generally cylindrical element (clamp sleeve) of the cam 20.

In particular, each of the limbs 16a-16j includes an aligned two-part firing mechanism: (1) a firing pin head 41a-41j (41e-41h not shown in FIG. 8) above (2) a part of a staple firing chamber 43a-43j (43a, 43e-43h not shown in FIG. 8). Such a firing mechanism is well known to those familiar with stapler design. Each of the firing pin heads is shorter in length than its corresponding staple firing chamber. In this embodiment, each firing pin head 41a-41j is positioned above and along the front two-third's (approximate) of its corresponding staple firing chamber 43a-43j.

As the cam 20 moves the stapler 10 from its open position to its closed position, the cam 20 comes into direct contact due to spring angle tension first with the tops of the staple firing chambers 43a-43j and then the tops of firing pin heads 41a-41j of the limbs 16a-16j. As the cam 20 moves along the length of the stapler 10, the cam 20 first encounters those parts of the staple firing chambers 43a-43j that are not topped by the firing pin heads 41a-41j. The tops of these initial sections of the staple firing chambers 43a-43j each include a bevel (also referred to as ramp) that rises towards the front end 14 of the stapler 10. The cam 20 causes each of the limbs 16a-16j to move from their open positions to their closed positions when the cam "climbs" the bevels of the staple firing chambers 43a-43j of the limbs 16a-16j.

FIG. 8 depicts the stapler 10 in its closed position. To move the stapler 10 into firing position, the control 22 is turned further in the clockwise direction. The turning of the control 22 causes the cam 20 to continue its movement along the length of the stapler 10, and in particular, along the tops of the firing pin heads 41a-41j of the limbs 16a-16j. The top of each of the firing pin heads 41a-41j has a lower or back section that begins with a bevel (also referred to as ramp) rising towards the front end 14 of the stapler 10. The cam 20 "climbs" the bevels of the firing pin heads 41a-41j towards the front end 14 of the stapler 10. The movement of the cam 20 on the firing pin heads 41a-41j forces each of the firing pin heads 41a-41j into its corresponding staple firing chamber 43a-43j. As the cam 20 advances along the stapler 10 towards its closure, the cam 20 is in constant contact due to spring angle tension with the firing pin heads 41a-41j of the limbs 16a-16j. The cam 20 applies greater pressure as it moves forward along the tops of the firing pin heads 41a-41j due to the bevels decreasing the distance between the cam and the respective limbs 16a-16j at a greater rate than the forward advancement of the cam 20.

As noted, the top of each limb 16a-16j includes a series of two bevels or ramps. In FIG. 8, only the two ramps 42d, 44d of limb 16d are clearly visible. The first ramp 42d is located generally near the base of the staple firing chamber 43d of limb 16d (i.e., the end of the limb 16d opposite to its staple firing chamber 18d). The first ramp 42d begins near the end of the limb 16d and rises slightly until the ramp 42d ends in a generally perpendicular falling off of the ramp 42d. The second ramp 44d follows the first ramp 42d in series along the top of the limb 16d, but on the firing pin head 41d. Particularly, the second ramp 44d begins where the first ramp 42d falls off and rises slightly before the second ramp 44d levels off to the horizontal for a short distance that ends in a stop that marks the beginning of the staple firing chamber 18d of the limb 16d.

The movement of the cam 20 along the length of limb 16d towards the front end 14 of the anvil is now described. In the open position of the exemplary stapler 10, the cam 20 is generally positioned around the base of the limbs 16a-16j. The turning of the control 22 causes the control screw 36 to rotate thereby moving the cam 20 towards the front end 14 of the anvil 12. As the cam 20 moves along the limb 16d (and the other limbs), the cam 20 encounters the first ramp 42d, slides along it, and exerts downward pressure as the cam 20 moves along. The downward pressure causes the staple firing chamber 18d of limb 16d to move from its open position about the front end 14 of the anvil 12 to a closer position about the front end 14 that is referred to as the "closed position". FIG. 8 specifically depicts the exemplary stapler 10 in its closed position.

To move the exemplary stapler 10 back to its open position from the closed position depicted in FIG. 8, the user may turn the control 22 in the opposite direction. In response, the control screw 36 turns in a direction opposite to its previous turning, and the cam 20 is caused to move away from the front end 14 of the anvil 12. Particularly, the cam 20 moves backwards down the first ramp 42d, and in moving off the ramp 42d, the cam 20 releases the pressure on the limb 16d (and the other limbs). The stapling arm 18d is released to return to its open position.

From its closed position depicted in FIG. 8, the exemplary stapler 10 may be moved to a firing position that causes the staples to be fired from the stapling arms 18a-18j. As noted, the cam 20 has been moved up the first ramp 42d of the limb 16d until the cam 20 encounters the perpendicular falling away of the first ramp 42d so as to attain the closed position for the exemplary stapler 10. To move the arms 16a-16j into firing position, the user continues to turn the control 22 in the direction that was used for moving the arms into the closed position. In response, the control screw 36 turns and causes the cam 20 to continue its movement towards the front end 14 of the anvil 12. In particular, the cam 20 encounters the second ramp 44d on the limb 16d and exerts pressure on the limb 16d. The cam 20 continues its movement and pressure as the control 22 is turned and until the cam encounters a stop 46d at the end of the second ramp 44d on the limb 16d. The stop 46d also marks the beginning the staple firing chamber 18d of the limb 16d. As a result of the exerted pressure of the cam 20 on the limbs 16a-16j, the stapling heads 118a-18j are caused to fire their respective staples.

In this embodiment 10, the firing of the staples may be characterized as a slow deformation of the staples as the cam 20 moves forward along the length of the stapler 10 towards its front end 14. As the cam 20 moves forward, more pressure is exerted so the staples are compressed or formed between the anvil and the stapling heads.

An embodiment of the inventions may include a feature particular to the control 22 so as to avoid overtightening. Such a control may allow only a certain amount of pressure when rotating to the closed position before the control then locks in that closed position until the direction of rotation is reversed. This is a feature that also may be found in some torque wrenches and screw guns to avoid overtightening.

Figure 9:
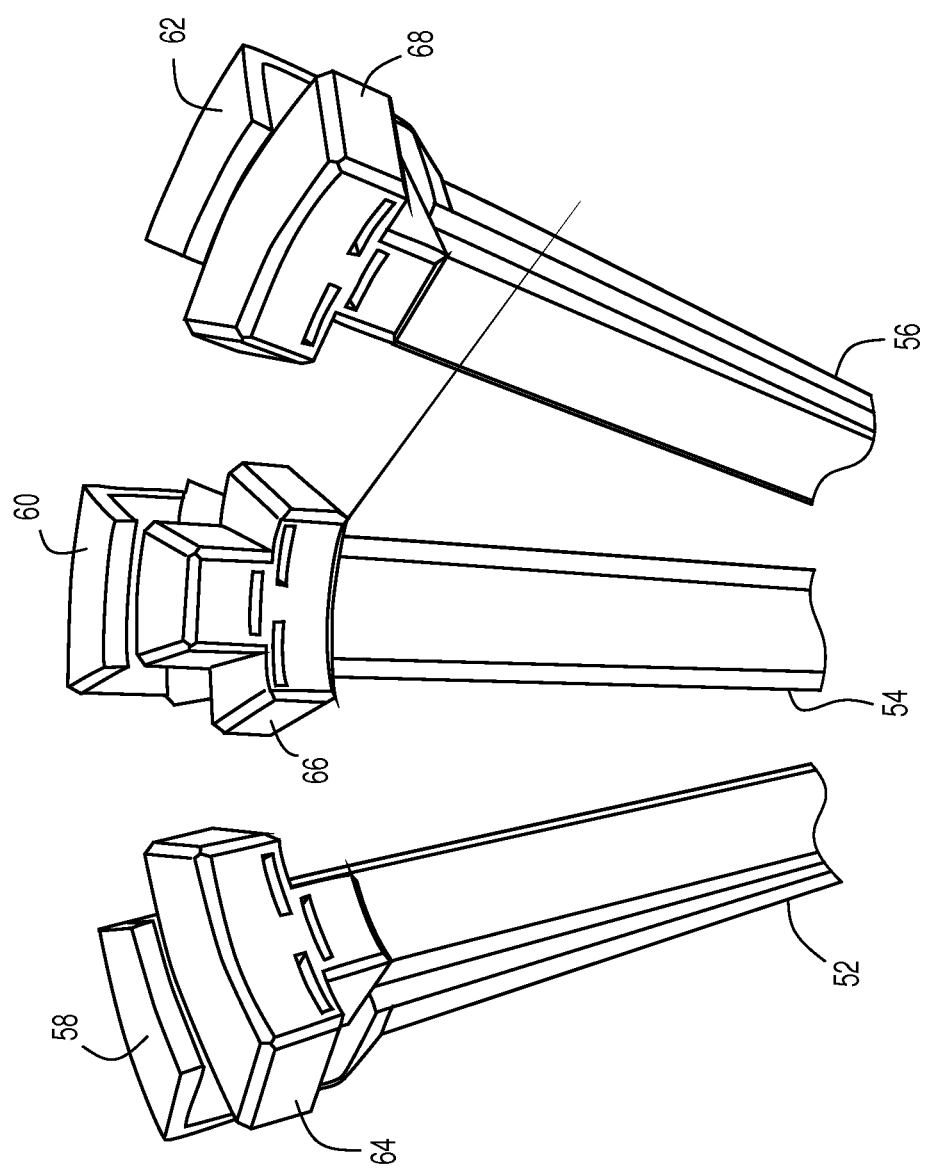
FIG. 9 is a drawing of three exemplary limbs of an exemplary embodiment of the invention.
Figure 10:
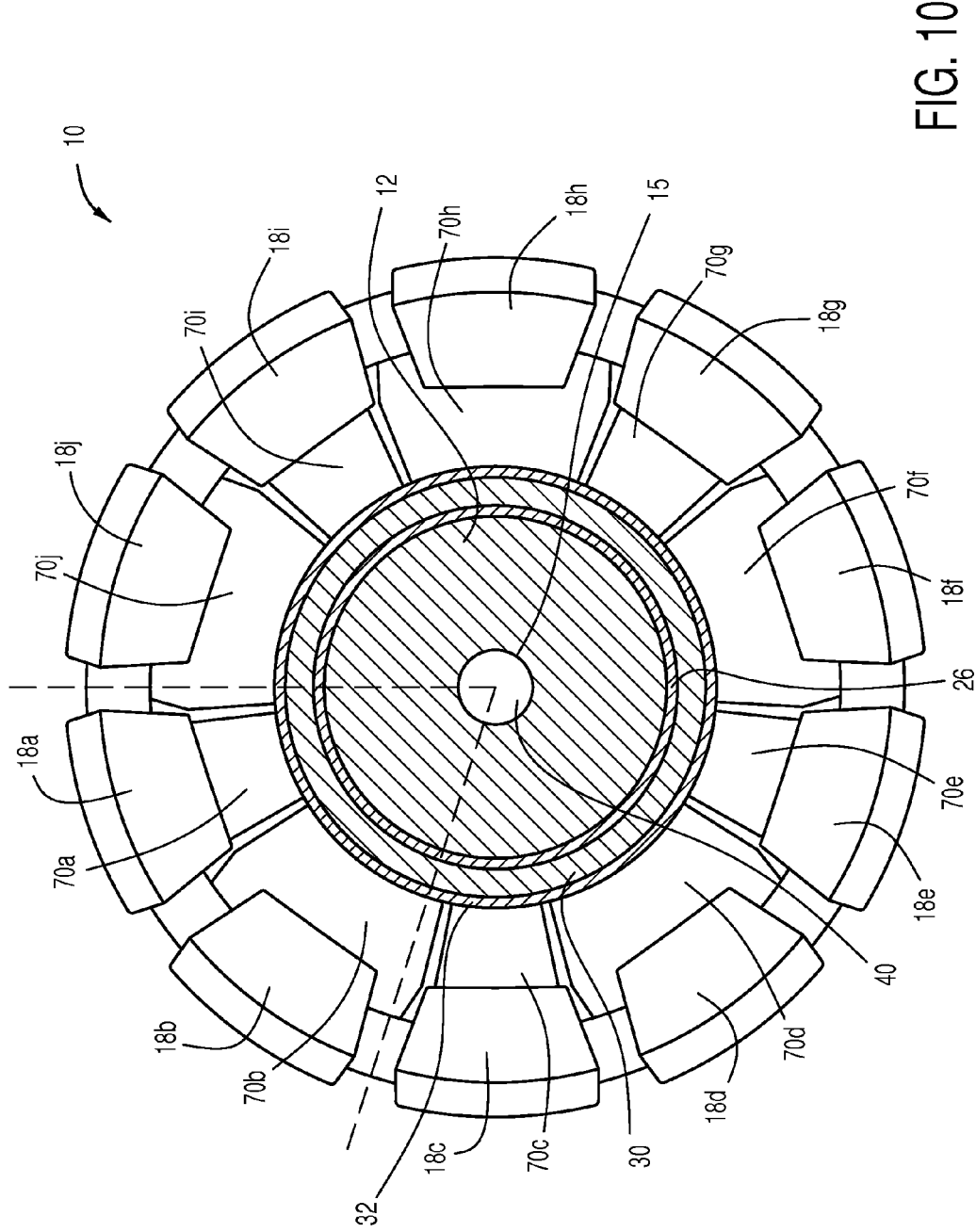
FIG. 10 is a radial cross section of the exemplary embodiment of FIG. 7.

Additional information about features of the limbs that may be used with the exemplary embodiment 10 (as well as other embodiments) is now provided by reference to FIGS. 9, 10 and 11.

FIG. 9 illustrates three exemplary limbs 52, 54 and 56 as may be used with the exemplary embodiment 10 or other embodiments. Each limb 52, 54, 56 includes a respective firing pin head 58, 60, 62. Each limb 52, 54, 56 is generally the same in terms of size, structure, functionality except for the pattern in which each limb 52, 54, 56 fires its staples and the staple firing chambers 64, 66, 68 that facilitate such patterned stapling. In this embodiment, three staples in two rows are fired from each limb 52, 54, 56, but in one of two patterns. The first pattern is two spaced apart staples in the top row and one staple in the bottom row. Limbs 52, 56 fire staples in the first pattern. The second pattern is one staple in the top row and two spaced apart staples in the bottom row. Limb 54 files staples in the second pattern.

In both patterns, the single staple is wider than the space between the staples in the other row. The result of these two firing patterns is that the limbs of the exemplary embodiment fire staples into two circumferential generally parallel but staggered rows. The pattern of the staples in the two rows may be referred to as "interleaved". Advantageously, the staggered rows of staples makes for a leak proof connection. The staples are all of the same size in this embodiment 10, but do not necessarily have to be so long as the leak proof connection is attained.

The exemplary embodiment 10 facilitates the use of the two patterns of three staples by including staple firing chambers where a staple firing chamber corresponds to a limb's firing pattern. For example, limbs 52 and 56 include respectively staple firing chambers 64, 68. Each staple firing chamber 64, 68 is a generally T-shaped element that allows room for the T-shaped first pattern of staples with two on top and one on bottom. Limb 54, on the other hand, has an "inverted" T-shaped staple firing chamber 66 as an element. Inverted T-shaped staple firing chamber 66 allows room for the inverted T-shaped second pattern of staples with one on top and two on the bottom.

In the exemplary stapler 10, the T-shaped staple firing chambers on the limbs alternate with the inverted T-shaped staple firing chambers. With an even number of limbs, the result is the limbs fire staples into the two circumferential generally parallel but staggered rows.

In the exemplary embodiment 10, the staple firing chambers of the limbs are configured to "mate" so the limbs 16a-16j in the closed and firing positions come together in a substantially closed circle around the front end 14 of the anvil 12. There is not much space between the staple firing chambers of the limbs when they are in their closed and firing positions.

FIG. 9 is used to explain how the staple firing chambers 64, 66, 68 may be made to match up. Staple firing chamber 64 is T-shaped. To the right of staple firing chamber 64, staple firing chamber 66 has an inverted T-shape. The right side of staple firing chamber 64 matches or fits together with the left side of staple firing chamber 66. Specifically, the right arm in the "T" of staple firing chamber 64 fits above the left arm of the inverted "T" of staple firing chamber 66 when their respective limbs are in the closed and firing positions. Similarly, the right arm of the inverted "T" of staple firing chamber 66 fits below the left arm in the "T" of the staple firing chamber 68, which is to the right of staple firing chamber 66, when their respective limbs are in the closed and firing positions. Advantageously, it is relatively easy for the staple firing chamber 64, 66, 68 to move out of their matched positions when their respective limbs move to an open position.

FIG. 10 provides a view of how the staple firing chamber of the limbs 16a-16j in the exemplary embodiment 10 match up to form a circle around the front end 14 of the anvil 12. FIG. 10 is a radial cross section of the exemplary embodiment 10. The center circle represents the core 40 in the anvil 12 for receiving the control screw 36 (although the control screw 36 may not extend all along the length of the core 40). Around the core 40, the front end 14 of the anvil 12 is depicted. In this embodiment 10, the anvil 12 has an outer diameter of about 27.5 mm.

A tubular graft 26 is sleeved about the anvil 12. In this embodiment 10, the cylindrical wall of the tubular graft 26 has a thickness of about 1.0 mm. When the tubular graft 26 is compressed as a result of the stapling connection to the end of the aorta 30 and the graft collar 32, the compressed tubular graft has a thickness of about 0.75 mm.

The circle 30 around the graft 26 represents the end of the dissected aorta. The end of the dissected aorta in this example has a thickness of 2.0 mm with a compression rate of about 30% or 1.4 mm when staple connected using the exemplary embodiment 10. The outermost circle 32 represents graft collar that may be placed around the end of the dissected aorta 30 prior to connection of the tubular graft 26 and the aorta 30. The graft collar 32 has a thickness of 1 mm prior to compression, but about 0.75 mm after.

The stapling heads 18a-18j of the limbs 16a-16j of the exemplary embodiment 10 are shown in their closed positions encircling the elements listed in the previous paragraph. There are ten (10) stapling heads 18a-18j in this embodiment 10. Other embodiments may also have 1 or more or less. Five (5) of the stapling heads 18b, 18d, 18f, 18h and 18j have T-shaped staple firing chambers 70b, 70d, 70f, 70h, and 70j. The other five (5) of the stapling heads 18a, 18c, 18e 18g, and 18i have inverted T-shaped staple firing chambers 70a, 70c, 70e, 70g, and 70i. The left arms of the T-shaped staple firing chambers 70b, 70d, 70f, 70h, and 70j fit over the respective right arms of the inverted T-shaped staple firing chambers 70a, 70c, 70e, 70g, and 70i. The right arms of the T-shaped staple firing chambers 70b, 70d, 70f, 70h, and 70j fit over the respective left arms of the inverted T-shaped staple firing chambers 70c, 70e, 70g, 70i, and 70a. As noted previously, the fit between the stapling heads 18a-18j is relatively close with hardly if any space between.

Figure 11B:
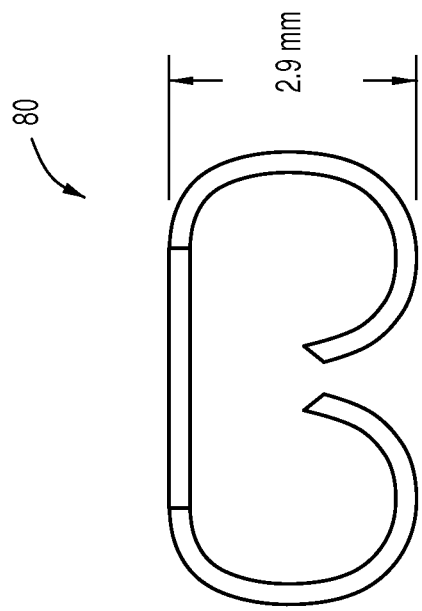
FIG. 11B is an exemplary embodiment of a formed staple that may be used with an exemplary embodiment of the invention.
Figure 11A:
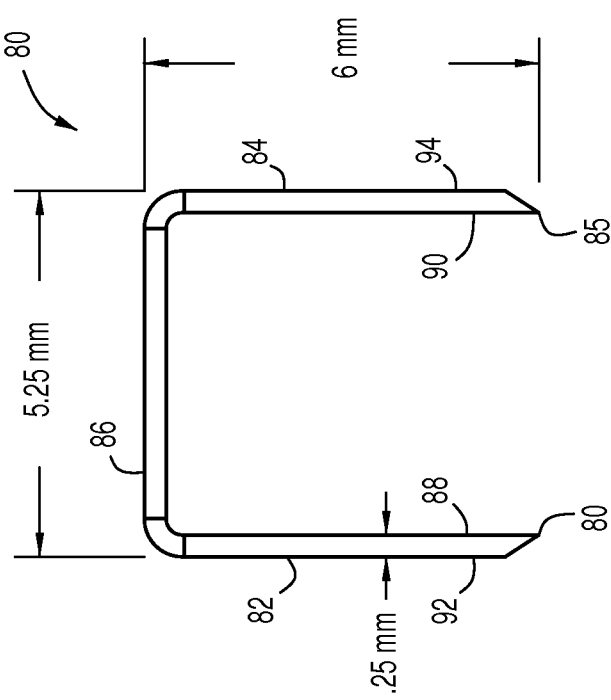
FIG. 11A is an exemplary embodiment of an unformed staple that may be used with an exemplary embodiment of the invention.

FIGS. 11A and 11B illustrate a staple 80 that may be used with the exemplary embodiment 10. Other connection means and differently sized or shaped staples may be used in other embodiments. FIG. 11A shows the staple 80 as it may be loaded into a staple firing chamber 70a-70j of a limb 16a-16j. Prior to stapling, the staple 80 may be referred to as "unformed"; after stapling, as shown in FIG. 11B, the staple 80 may be referred to as "formed".

The unformed staple 80 is generally U-shaped having two generally parallel sides 82, 84 and a top 86 generally perpendicular to the sides 82, 84. There are ends 83, 85 of the sides 82, 84 of the staple 80 opposite to the top 80. The ends 83, 85 also may be referred to as "prongs" or "tips". These ends 83, 85 are cut at an angle of about 45 degrees such that the inside sides 88, 90 of the sides 82, 84 of the staple 80 are slightly longer than the outside sides 92, 94. There may be advantages to the ends 83, 85 of the staple 80 having angled cut ends. When the staple 80 is "stapled", it is forced through the materials it is connecting. The angled ends 83, 85 may work their way through the materials easier than blunt ends. Also, when the staple 80 is "stapled", it encounters the anvil 12 after the staple has been forced through the materials. The relatively forceful encounter with the anvil 12 may cause the sides 82, 84 of the staple 80 to change shape. The force may distend the sides 82, 84 into a semi-circular shape as may be seen in FIG. 11B. In particular, the sides 82, 84 may distend in a curved manner outwards from their perpendicular relationship to the top 86 of the staple 80. The formed staple 80 therefore may be wider than the unformed staple. In addition, the ends 83, 85 of the sides 82, 84 staple 80 bend inward, towards each other and then towards the inside top of the staple as shown in FIG. 11B. The bending of the staple sides, and particularly the ends 83, 85 may aid in the security of the connection of the materials that are stapled.

Exemplary staple 80 is made all of one material (titanium), but does not necessarily have to be.

The exemplary staple 80 is sized as follows, but as noted, other sizes of staples may be used in other embodiments. In the unformed staple 80, the sides 82, 84 are 6 mm in length. The top 86 of the staple 80 is 5.25 mm wide. The overall thickness of the staple 80 is 0.25 mm. When the staple is formed, the width of the staple 80 is slightly larger than its original size and its length is 2.9 mm. The size of the staple 80 may correspond to the elements the staple 80 connects. In this example, the formed staple 80 is long enough (2.9 mm) to connect the tubular graft 26, the end of the aorta 30, and graft collar 32, which in their compressed state have a total diameter of about 2.9 mm.

FIG. 12 illustrates an exemplary result of use of the exemplary stapler 10. Missing from the illustration is the stapler 10 itself, which is not shown in FIG. 12 presumably because the exemplary stapler 10 has been removed from the operative field. The use of the exemplary stapler 10 has resulted in one end of the dissected aorta 30 having been connected via two circumferential rows of staples 96a, 96b between the graft collar 32 on the outside of the end of the dissected aorta 30 and the tubular graft 26 on the inside. The two circumferential rows of staples 96a are spaced about _ mm apart from each other. In each row 96a, 96b, there are spaces between staples. The rows 96a, 96b, however, are staggered in their patterns so that a space in a staple row 96a, 96b is "covered" by a staple in the opposite row. In this embodiment, the staples are wider than the space between staples. Thus, the staggered pattern allows for a leak-free connection between the end of the aorta 30 and the tubular graft 26.

The inventions also include methods of anastomosis. An exemplary method 100 is now described with reference to the flow diagram shown in FIG. 13. The exemplary method 100 makes use of the exemplary stapler 10 previously described, but other embodiments may be used.

The exemplary method 100 may begin with actions that may be optional depending on the circumstances relating to checking and/or setting up of the exemplary stapler 10. For example, to begin the method, the user may check whether the exemplary stapler 10 is in its "open" position (i.e., limbs away from the anvil). In action 110, if the exemplary stapler 10 needs to be "opened", then the user may actuate the control to cause the exemplary stapler to be in its "open" position. In an embodiment, the control may be a "fire and release knob" that is turned to a fully counter-clockwise position to accomplish opening of the exemplary stapler 10.

As another example of actions that may be optional to the exemplary method 100, the user may check whether the exemplary stapler 10 needs to be loaded with staples. If staples need to be loaded, then in action 120 the staples may be inserted into the respective firing cavities in the stapling tops. In the exemplary embodiment 10, the staples may be individually hand-loaded into the stapler 10. Other embodiments may automatically load staples, or may make use of stapler cartridges, which may be manually or automatically loaded. The order of the optional actions 110, 120 with respect to each other and/or to the other actions of the method 100 may vary from embodiment to embodiment, and should not be considered as restricted to the order presented herein.

The exemplary method 100 includes the action of positioning a tube to fit around a cylindrical anvil of a circular stapler. Specifically, in action 130, a DACRON® graft tube may be slid over the anvil. In the exemplary method 100, most if not all of the tube is sleeved over the anvil of the exemplary stapler 10 so that a segment of the tube is relatively close to if not substantially next to the front end of the anvil of the stapler 10. Action 130 of this exemplary method also includes securing the tube to the anvil by releasably tying the tube to the anvil. Other embodiments may not require this tying action and/or may secure the tube in other ways.

Figure 13:
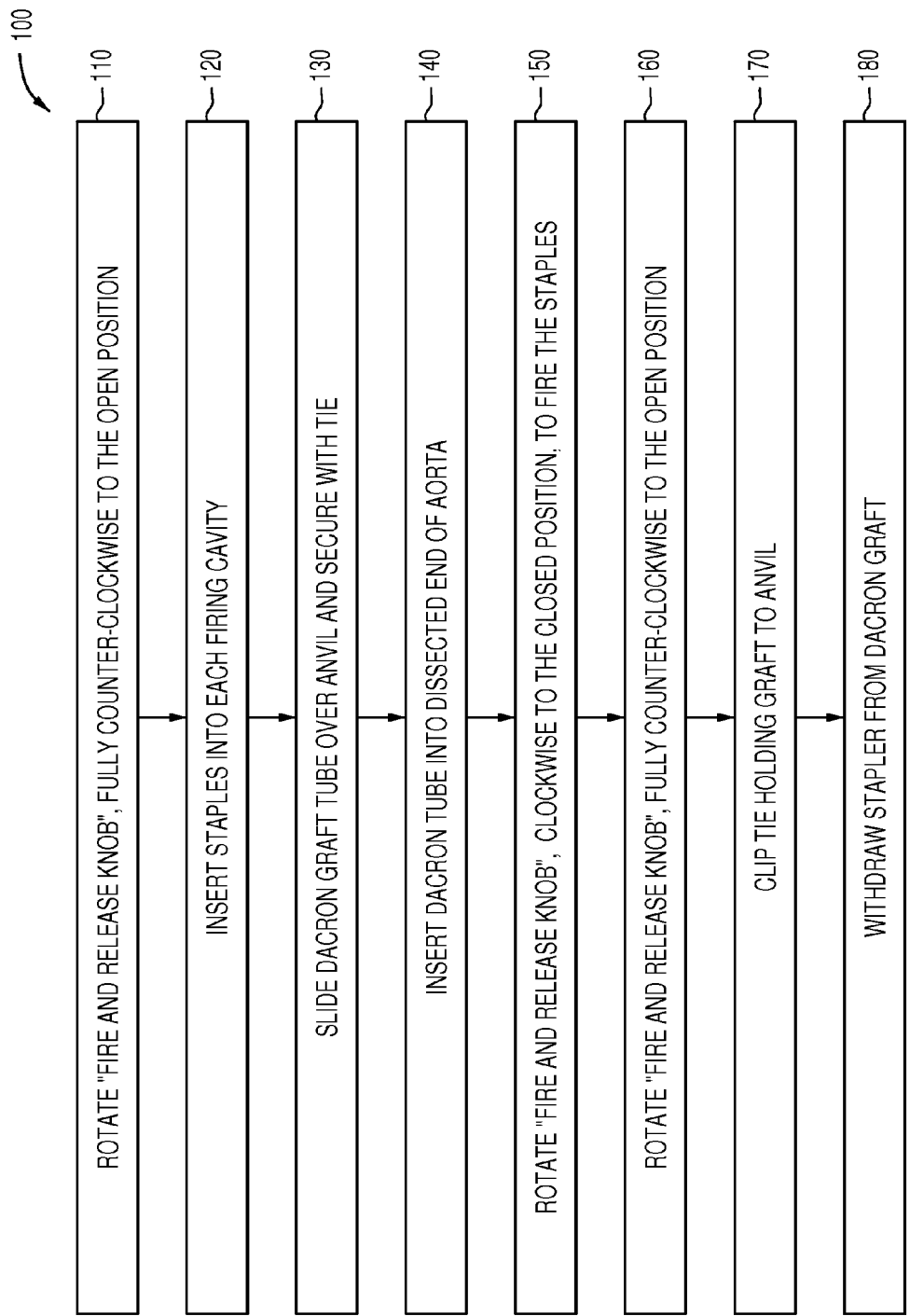
FIG. 13 is a flow diagram illustrating an exemplary embodiment of the invention.

In action 140 of FIG. 13, the stapler 10 is introduced into the operative field, and specifically, the graft tube on the anvil is inserted at least partially into a dissected end of the aorta. After insertion, a segment of the graft tube underlies a part of the dissected end of the aorta to form an overlap between the graft tube segment and the end part of the dissected aorta.

In action 150, the exemplary stapler 10 is used to make the leak-free connection between the graft tube and the end of the dissected aorta. Particularly, in this embodiment, the control (also referred to as the fire and release knob) is turned in a clockwise direction so that the limbs of the stapler move into their closed positions around the overlap. The control then is turned further clockwise to fire the staples into the overlap. In this embodiment, the firing of the staples causes each staple to pierce the overlap and to at least partially close behind it by an inward movement of each leg of a staple when it encounters the anvil. The firing position of the stapling heads may be characterized in this embodiment as a radial distribution about the overlap of the graft tube and the end of the dissected aorta. The staples may be fired so that the result is two parallel rows of staples around the overlap. The rows of staples (and the materials they compress) form a leak-free connection between the tube and the dissected end of the aorta.

To remove the stapler from the operative field, in action 150 the exemplary method provides for the control of the stapler to be rotated in a counter-clockwise direction to open the limbs of the stapler. In optional action 170, any tie and/or other means of securing the graft tube to the anvil of the stapler is undone or unsecured so the anvil may be withdrawn from the graft tube. In action 180, the stapler is removed so the graft tube remains in its leak-free connection to the dissected end of the aorta.

As noted, an exemplary embodiment of the invention may be used in an anastomosis to connect one end of a tubular graft in a leak-free connection with an end of a dissected aorta. The respective other ends of the tubular graft and the dissected aorta may also need to be connected in a leak-free manner, and such connection may be accomplished in any appropriate manner and/with any appropriate device. For example, the ends not connected according to the invention may be connected by suturing or any other method of bonding.

CONCLUSION

The exemplary embodiments of the present inventions were chosen and described above in order to explain the principles of the invention and their practical applications so as to enable others skilled in the art to utilize the inventions including various embodiments and various modifications as are suited to the particular uses contemplated. The examples provided herein are not intended as limitations of the present invention. Other embodiments will suggest themselves to those skilled in the art. Therefore, the scope of the present invention is to be limited only by the claims below.

The invention claimed is:

1. An apparatus for anastomosis, comprising:
an anvil having a length from a front end and defining a longitudinal axis;
stapling limbs disposed circumferentially about and along the length of the anvil, each stapling limb having stapling functionality at its limb end corresponding to the front end of the anvil and defining one of at least two complementary stapling patterns in an alternating configuration around the anvil;
each limb end being disposed for movement from an open position at a distance from the front end of the anvil to a closed position closer to the front end of the anvil, such that the complementary stapling patterns of adjoining stapling limbs are disposed in a mated configuration when the stapling limbs are in the closed position, wherein the complementary stapling patterns comprise alternating T-shaped and inverted T-shaped patterns, and wherein the mated configuration is defined such that a stapling limb defining a T-shaped pattern is engaged with a stapling limb defining an inverted T-shaped pattern;
a cam disposed for causing movement of each limb end from its open position to its closed position;
a rotary control rotatable about the longitudinal axis and capable of being selectively activated to cause the cam to cause the movement of each limb end to its closed position;
the anvil being capable of receiving a graft for connection to a vessel, and
the anvil with the graft being insertable at least partially into a portion of the vessel to create an overlap positioned on the anvil; and
the rotary control capable of being activated to cause the cam to cause each limb in its closed position to fire at least a staple perpendicular to the longitudinal axis into the overlap on the anvil to make a connection between the vessel and the graft at the overlap, such that stapling functionality of adjoining stapling limbs is configured to fire the staples in a staggered configuration.

2. The apparatus of claim 1, wherein the connection comprises a leak-proof connection.

3. The apparatus of claim 1, wherein staples are capable of being fired into the overlap to form two parallel rows in the overlap with staples of each row being staggered with respect to staples of the other row.

4. The apparatus of claim 1, wherein staples are capable of being fired into the overlap all at once.

5. The apparatus of claim 1, wherein the stapling limbs are disposed in pairs with each of the limb ends in a pair capable of firing three staples in two rows into the overlap.

6. The apparatus of claim 5, wherein a first limb end of the pair fires a staple into a top row and two staples into a bottom row, the two staples in the bottom row being spaced apart, and the staple in the top row positioned parallel at least in part to the space between the two staples in the bottom row; and
wherein a second limb of the pair fires two staples into a top row and one staple into a bottom row, the two staples in the top row being spaced apart, and the staple in the bottom row positioned parallel at least in part to the space between the two staples in the top row.

7. The apparatus of claim 1, wherein the cam is also disposed for causing a movement of each limb end from its closed position to its open position; and
wherein the control is also capable of being selectively activated to cause the cam to cause the movement of each limb end to its open position.

8. The apparatus of claim 1, wherein the graft comprises a tubular graft for connection to the vessel.

9. The apparatus of claim 1, further comprising a tie for securing the graft to the anvil.

10. The apparatus of claim 9, wherein the anvil defines a contour for securing the graft.

11. The apparatus of claim 10, wherein the contour comprises a circumferential groove.

12. The apparatus of claim 1, further comprising:
a strip of material for positioning over at least a segment of the portion of the vessel that is included in the overlap prior to the firing of staples into the overlap,
whereby the strip of material is connectable to the overlap by the fired staples.

13. The apparatus of claim 1, wherein the stapling limbs are configured to position tops of the staples perpendicular to the longitudinal axis.

14. The apparatus of claim 1, wherein the apparatus comprises ten or more stapling limbs, and wherein each stapling limb supports at least one staple.

15. The apparatus of claim 1, wherein the complementary stapling patterns comprise a first pattern and a second pattern, and wherein the mated configuration is defined such that a protruding portion of a stapling limb having the first pattern cooperates with a recessed portion of a stapling limb having the second pattern.

16. The apparatus of claim 1, wherein each stapling limb comprises two radially extending ramped portions, such that longitudinal advancement of the cam along the first ramp causes the limb to move to a closed position and that longitudinal advancement of the cam with the second ramp causes the limb to fire at least one staple.

17. A device for leak-free fastening of at least two tubular elements, comprising:
a cylindrical central base having a fastening end and defining a longitudinal axis;
a fastening mechanism comprising a plurality of stapling limbs, each stapling limb defining one of at least two complementary stapling patterns in an alternating configuration positioned about the fastening end of the base and capable of moving between an open position about the fastening end, a closed position about the fastening end such that the complementary stapling patterns of adjoining stapling limbs are disposed in a mated configuration, and a firing position about the fastening end, wherein the complementary stapling patterns comprise alternating T-shaped and inverted T-shaped patterns, and wherein the mated configuration is defined such that a stapling limb defining a T-shaped pattern is engaged with a stapling limb defining an inverted T-shaped pattern,
a rotary control rotatable about the longitudinal axis and capable of being selectively activated to cause the movement of the fastening mechanism from the open position to the firing position;
the open position of the fastening mechanism allowing an entire length of a tubular first element to be sleeved relatively snugly around the base, and
also for insertion of the fastening end of the base into a portion of a tubular second element to form an overlap between a part of the sleeved tubular first element and the portion of the tubular second element; and
the fastening mechanism responsive to a firing actuation of the rotary control
to move from the open position into the firing position about the fastening end and close to the overlap, and
to make a circumferential leak-free fastening between the first and second tubular elements at the overlap by driving fasteners perpendicular to the longitudinal axis such that stapling functionality of adjoining stapling limbs is configured to fire the staples in a staggered configuration.

18. The device of claim 17, wherein the fastening mechanism is responsive to an opening actuation to move away from the firing position to allow for withdrawal of the fastened first and second tubular elements from the base.

19. The device of claim 17, wherein the fastening mechanism is responsive to a positioning actuation to move from the open position into a closed position about the fastening end and close to the overlap.

20. The device of claim 17, wherein the complementary stapling patterns comprise a first pattern and a second pattern, and wherein the mated configuration is defined such that a protruding portion of a stapling limb having the first pattern cooperates with a recessed portion of a stapling limb having the second pattern.

21. The device of claim 17, wherein each stapling limb comprises two radially extending ramped portions, such that longitudinal advancement of the cam along the first ramp causes the limb to move to a closed position and that longitudinal advancement of the cam with the second ramp causes the limb to fire at least one staple.

* * * * *